United States Patent [19]

Shikowitz

[11] Patent Number: 4,925,736

[45] Date of Patent: May 15, 1990

[54] TOPICAL HEMATOPORPHYRIN

[75] Inventor: Mark J. Shikowitz, Dix Hills, N.Y.

[73] Assignee: Long Island Jewish Medical Center, New Hyde Park, N.Y.

[21] Appl. No.: 215,837

[22] Filed: Jul. 6, 1988

[51] Int. Cl.$^5$ .......................... A61K 31/40; A61K 7/48; A61L 15/04

[52] U.S. Cl. .................................... 424/449; 514/185; 514/969; 540/145

[58] Field of Search ............... 424/401, 434, 435, 436, 424/449; 514/185, 410, 969; 540/145

[56] References Cited

U.S. PATENT DOCUMENTS

| | | | |
|---|---|---|---|
| 4,649,151 | 3/1987 | Dougherty et al. | 514/410 |
| 4,696,905 | 9/1987 | Aoyama et al. | 436/64 |
| 4,753,958 | 6/1988 | Weinstein et al. | 514/410 |

FOREIGN PATENT DOCUMENTS 43555  10/1963  France .............................. 514/185

OTHER PUBLICATIONS

Beani et al., "Problems poses par l'utilisation therapeutique des photosensibilisateurs en dermatologie", Biochimie, vol. 68, pp. 905–912 (1986).

Abramson et al., "Thermal Effects of Photodynamic Therapy on the Larynx", Arch. Otolaryngol. Head Neck Surg., vol. 113, pp. 854–858 (Aug. 1987).

Abramson et al., "The Pathologic Affects of Photodynamic Therapy on the Larynx", Arch. Otolaryngol Head Neck Search, vol. 114, pp. 33–39 (Jan. 1988).

Shikowitz et al., "Hematoporphyrin Derivative Therapy of Papillomas", Archives of Otolaryngology Head Neck Surg., vol. 112, pp. 42–46, (Jan. 1986).

Amano et al., "Intratumor Injection As A More Effective Means of Porphyrin Administration For Photodynamic Therapy", Journal of Urology, vol. 139, pp. 392–395 (Feb. 1988).

Dougherty et al., "The Structure of the Active Component of Hematophorphyrin Derivative", Porphyrin Localization and Treatment of Tumors, pp. 301–314, Copyright 1984.

Shikowitz et al., "Molecular Analysis of Cottontail Rabbit Papillomavirus–induced Papillomas Treated with Hematoporphyrin Photodynamic Therapy", Cancer Cells 5/Papillomaviruses, pp. 411–416 (1987).

Gomer et al., "Expression of Potentially Lethal Damage in Chinese Hamster Cells Exposed to Hematoporphyrin Derivative Photodynamic Therapy", Cancer Research, vol. 46, pp. 3348–3352 (Jul. 1986).

Benson, Jr., "Treatment of Diffuse Transitional Cell Carcinoma in Situ by Whole Bladder Hematoporphyrin Derivative Photodynamic Therapy", Journal of Urology, vol. 134, pp. 675–678 (Oct. 1985).

Gluckman et al., "Photodynamic Therapy", Arch. Otolaryngol. Head Neck Surg., vol. 112, pp. 949–952 (Sep. 1986).

Pathak et al., "The Nature and Molecular Basis of Cutaneous Photosensitivity Reactions to Psoralens and Coal Tar", Journal Invest. Der., vol. 80, No. 6, pp. 66s–73s (1983).

Grossman, "Diagnosis and Treatment of Bladder Carcinoma", Comprehensive Therapy, vol. 12, No. 8, pp. 42–47 (1986).

Zincke et al., "Review of Mayo Clinic Experience with Carcinoma in Situ", Supplement to Urology, vol. 26, No. 4 (1985).

McCullough et al., "Development of a Topical Hematoporphyrin Derivative Formulation: Characterization of Photosensitizing Effects in Vivo", Journal of Invest. Derm., vol. 81, No. 6, pp. 528–532 (1983).

McCullough et al., "Development of a Topical Hematoporphyrin Derivative (HPD) Formulation and Characterization of its Photosentizing Effects in Guinea Pig Skin", Abstract, vol. 78, No. 4, p. 356; Journal Invest. Derm.; and Clinical Research, vol. 30, No. 1, p. 158A (1982).

Montrecola et al., "Topical Hematoporphyrin plus UVA for Treatment of Alopecia Areata", Photodermatology, vol. 4, pp. 305–306 (1987).

Primary Examiner—John Kight, III
Assistant Examiner—Carlos Azpuru
Attorney, Agent, or Firm—Kenyon & Kenyon

[57] ABSTRACT

A topical hematoporphyrin composition, the method for its production, and a method for its use in the treatment of human papillomavirus disease are described. The hematoporphyrin composition is capable of being absorbed by diseased tissue, thus enabling destruction of the tissue upon exposure to 625 to 635nm light.

37 Claims, No Drawings

TOPICAL HEMATOPORPHYRIN

BACKGROUND OF THE INVENTION

1. Field of the Invention

This invention pertains to the field of treatment of human papillomavirus disease using photodynamic therapy. More specifically, it relates to the use of a topical hematoporphyrin composition that can be absorbed into diseased tissue thus enabling application of phototherapy to localized skin and mucosal growths.

2. Description of the Prior Art

Photochemotherapy is a rapidly developing method for treatment of malignant diseases in humans and animals. Photodynamic therapy (PDT) involves destruction of tissue that retains a photosensitizing agent by exposing the tissue to light of the appropriate wavelength, most commonly in the red area between 625 and 635 nm. The agent hematoporphyrin derivative (HPD), or its active component dihematoporphyrin ether (DHE), has been found to selectively localize in abnormal tissue such as malignancies or papillomas. As such, HPD or DHE (hereinafter referred to as HPD/DHE) can be injected intravenously and allowed to migrate to tumorous sites. Subsequent exposure of the site to light of the appropriate wavelength causes destruction of the tumor, most likely by a process involving production of excited metastable molecular oxygen and toxic oxygen radicals, which lead to disruption of the cell membranes by lipid oxidation and protein sulfhydryl oxidation.

Although photodynamic therapy has been used successfully for the treatment of metastatic breast tumors, endometrial carcinomas, bladder tumors, malignant melanoma, Kaposi's sarcoma, basal cell carcinoma, chondrosarcoma, squamous cell carcinoma, prostate carcinoma, laryngeal papillomas, mycosis fungoides, superficial cancer of the tracheobronchial tree, and cutaneous/mucosal papilloma, it still has its drawbacks. The most predominant drawback is the fact that systemic injection of a photosensitizing agent requires the patient to avoid bright light, especially sunlight, for periods of 4 to 6 weeks. Consequently, the use of HPD/DHE has been limited to patients with severe disease.

As an alternative to intravenous injection of photoreactive agents, various researchers have attempted to directly inject HPD/DHE into tumors. Amano, et al., Journal of Urology 139, 392 (1988) have reported that high porphyrin levels in HPD injected tissue, and low porphyrin levels in surrounding tissues, indicate that such a method may be a viable alternative in cases where there are single lesions that are directly accessible.

Papilloma diseases, however, are often associated with multiple skin/mucosal growths which are frequently inaccessible to injection. Therefore a composition that could be applied topically, possibly even by the patients themselves prior to receiving the appropriate light treatment, would significantly enhance the usefulness of HPD/DHE therapy. McCullough, et al. Journal of Investigative Dermatology 81, 528 (1983) have reported the development of a topical lyophilized hematoporphyrin derivative formulation for the treatment of psoriasis and other cutaneous diseases. Using HPD in conjunction with azone and N-methylpyrrolidone, they demonstrated that exposure of a treated area of guinea pig skin to red light resulted in significant erythema and inhibition of epidermal DNA synthesis.

Although such topical hematoporphyrin formulations are useful in the treatment of cutaneous and subcutaneous diseases, HPD/DHE has not been found to be generally useful for the treatment of papillomavirus disease because of its inability to penetrate the tissue sufficiently to allow complete destruction of the growths. Utilization of HPD or DHE in aqueous solution on papillomavirus induced warts is not effective because the solutions are incapable of penetrating the lesions. Rather, they merely dry on the surface. Combinations of lyophilized HPD or DHE with commercially available carrying agents for topical application also fail, due either to loss of activity as a result of lyophilization of the HPD/DHE, or because the HPD/DHE is only partially soluble and the particulate portion does not penetrate the papilloma or normal skin. As a result, although photodynamic therapy using intravenous HPD derivative has proven useful for treatment of laryngeal papillomas, cutaneous experimental and naturally occurring lesions, and other forms of tumors, currently available therapies such as removal by use of $CO_2$ laser or surgical excision are more commonly used with accessible growths.

The above problems associated with the prior art use of photodynamic treatment are overcome in the present invention by the development of a topical hematoporphyrin derivative formulation that can be applied directly to tumorous sites. The active compounds of the HPD/DHE are transported into the growth, which, upon exposure to red light with a wavelength of 625 to 635 nm, is destroyed.

SUMMARY OF THE INVENTION

The invention is based upon the discovery that the light sensitivities encountered by use of systemic photodynamic therapy can be alleviated by use of HPD locally at the site of tumorous growth. It is further based on the discovery that HPD/DHE which is not naturally capable of diffusing into epithelial malignancies or papillomas, can be combined in a form that allows such diffusion and subsequent light treatment of the site to destroy the treated growth without the drawback of toxic systemic photosensitization.

DETAILED DESCRIPTION

The present invention provides a non-lyophilized composition for photodynamic therapy which comprises a photoreactive agent such as one or more hematoporphyrins dispersed in a carrier vehicle which is capable of deep penetration when applied to mammalian skin/mucosa. By "deep penetration" it is meant that the carrier vehicle allows the photoreactive agent to penetrate the diseased tissues sufficiently to allow substantial destruction of the particular growths to be treated. Acceptable carrier vehicles are those which are well known to those skilled in the art as being capable of penetrating the skin and are commercially available as a variety of hydrophilic gels or creams.

The present invention also relates to a process for preparing a topical non-lyophilized composition for photodynamic therapy wherein an aqueous solution of one or more photoreactive agents such as HPD/DHE are concentrated but not brought to dryness and thereafter rediluting in the penetrating topical carrier vehicle.

The concentration of the aqueous solution is preferably accomplished by slow evaporation with a constant, mild agitation under constant cooling. It is most preferred that the agitation of the aqueous solution during the slow evaporation step and the redilution step be carried out such that the constant, mild agitation results in a vortexing motion of the solutions. By "vortexing" it is meant a whirling motion of the solution such that a depression is formed in the center, i.e. a whirlpool. In preferred embodiments, the evaporation continues until the volume of the aqueous solution is from about 20 to about 25 percent of its original volume. It is also preferred that the original concentration of photoreactive agent in the aqueous solution be from about 1 to about 7.5 g/ml, and that the resulting concentration be brought back to approximately its original volume with the carrier vehicle.

HPD/DHE is commonly available in the form of a 2.5 mg/ml aqueous solution. Thus, in a most preferred embodiment, the 2.5 mg/ml solution of HPD/DHE is slowly evaporated under vacuum with constant cooling and vortexing until its volume is 20–25% of its original volume. It is then brought back to its original volume by dilution with a suitable topical carrier vehicle. The resulting topical composition may be stored by placing the same in a dark container and refrigerating. Thereafter it may be applied to an area of mammalian skin or mucosa which is to be treated. The HPD/DHE composition can be applied directly or through the use of a cutaneous bandage or patch.

The region is subsequently irradiated in a known manner using light in the red spectrum, preferably having a wavelength of from about 625 to about 635 nm. The light treatment causes the destruction of the diseased area. The above-mentioned treatment is preferred for use in the treatment of papillomavirus disease. However, it may be used to treat a wide variety of lesions, tumors, etc. Such treatments are contemplated to be within the scope of the present invention.

Suitable topical carrier vehicles capable of deep penetration when applied to mammalian skin/mucosa include a variety of well known topical gels, hydrophilic ointments or creams which are commercially available as bases for incorporation of various active ingredients in extemporaneously compounded formulations. Such carrier vehicles typically include one or more of alcohol, propylene glycol, higher ethylene glycol polymers such as polyethylene glycol, polysorbate 20,40 and or 80, polyoxyethylene lauryl ether, glycerine, urea, sodium laurel sulfate, waxes, gums and the like. Most of the commerically available carrier vehicles which are suitable for use in the present invention have a high alcohol content (i.e., at least 25% alcohol by weight).

Two suitable carrier vehicles that are particularly preferred for use in the hematoporphyrin composition of the present invention are dimethylsulfoxide (DMSO) and Pharmasolve TM, a commercially available carrier distributed by Young Pharmaceutical Inc., containing 54% by weight SD alcohol, the remainder comprising propylene glycol, purified water, polyoxyethylene lauryl ether and dioctyl sodium sulfosuccinate.

Other suitable carrier vehicles which are commercially available include hydrophilic ointments available from a variety of suppliers. Hydrophilic ointment typically comprises 25% white petrolatum, 25% stearyl alcohol, 12% propylene glycol and 1% sodium lauryl sulfate with methyl and propyl parabens. Other commerically available products contemplated for use in the present invention include lotions such as Neutrogena Vehicle/N TM; Neutrogena Vehicle/N Mild TM; E-Solve TM and C-Solve TM (Syosset); Aquaphor TM (Beiersdorf); Unibase TM (Parke-Davis); Polysorb Anhydrous TM (Fougera); Azone TM (Nelson Research) alone or in various alcohol-containing solutions; Velvachol TM, Dermovan TM and Nutraderm TM (all available from Owen); Heb Cream Base TM (Barnes-Hind); Eucerin TM (Beiersdorf); and mixtures thereof. The above-mentioned products are provided as examples only, and the list is not meant to be exclusive. Many variations of the above, along with other suitable topical carrier vehicles will suggest themselves to those skilled in the art in light of the foregoing detailed description. All such obvious variations are contemplated to be within the scope of the appended claims.

DESCRIPTION OF THE PREFERRED EMBODIMENT

The following examples are directed to embodiments of the present invention and are submitted for illustrative purposes only. The examples are not to be construed as limiting the scope of the invention set forth in the claims.

EXAMPLE 1

PRODUCTION OF TOPICAL DHE COMPOSITION

An aqueous (2.5 mg/ml) solution of DHE was allequoted in 2 cc amounts and placed in separate tubes. The DHE was cooled to 10° C.±5° and a vacuum of 20–35 mm Hg applied. The solution was slowly evaporated under constant cooling at 10° C.±5 with vortexing (Evapotec, A Haake Buchler, N.J.) until a final volume of approximately 20% of the original volume was obtained. The concentrated DHE was rediluted to its original volume in Pharmasolve in an ice bath with constant vortexing. The solution was then placed in a dark container and kept refrigerated.

EXAMPLE 2

ABSORPTION OF HPD/DHE TOPICAL COMPOSITION

The backs of rabbits were shaved and multiple areas measuring 4 cm in diameter were outlined. One region was always kept as a control region. One region received the DHE-Pharmasolve produced as described in Example 1, a second region received DHE-DMSO produced by the same method as set forth in Example 1, but substituting DMSO for Pharmasolve, a third region received Pharmasolve alone, and a fourth received DMSO alone. Each region was irradiated with 630 nm light from an Argon pump dye laser at 9 Joules. Following this, each region was observed. No change was observed in the regions of normal skin and plain solvent (DMSO or Pharmasolve), while the regions treated with DHE-Pharmasolve or DHE-DMSO changed color to a darker brown. Attempts to wash these regions with soap and water or alcohol failed to change the color. At 48 hours the regions that were treated with the DHE compositions and irradiated with light demonstrated a significant hyperemia reaction. This continued over the next 48 hours and eventually resolved (disappeared) at 1 week post treatment. This demonstrated absorption and reaction at the cutaneous level for the topical agent.

EXAMPLE 3

ABSORPTION OF DHE TOPICAL COMPOSITION

A second experiment was conducted using six regions on the back of a rabbit. DHE topical compositions were produced according to the method set forth in Example 1.

The regions were treated as follows:
A - DMSO-DHE+light
B - DMSO-DHE—no light
C - DMSO alone+light
D - Pharmasolve-DHE+light
E - Pharmasolve-DHE—no light
F - Pharmasolve alone+light Each solution was allowed to absorb for 3 hours and treated with 630 nm red light as described in Example 2. Regions A and D immediately turned darker brown. No change occurred in regions B, C, E and F. At 48 hours there was significant hyperemia of regions A and D and no reaction in the regions that did not receive red light or where solvents alone were placed.

EXAMPLE 4

TREATMENT OF PAPILLOMAS

Papillomas were induced with cotton tail rabbit papillomavirus (CRPV) on the back of a Dutch belted rabbit. Two were used as controls, and two regions of normal skin acted as positive controls. Two papillomas were treated with DHE-DMSO produced according to the method of Example 1, and the other two received DHE-Pharmasolve (also produced as set forth in Example 1). Light from a laser (630 nm) was administered to one papilloma with DHE-DMSO and one with DHE-Pharmasolve. The other two remained in the dark as controls.

After 3 weeks, complete regression was observed of the papilloma treated with DHE-Pharmasolve and exposed to 630 nm light, and partial regression was observed with the red light exposed papilloma treated with DHE-DMSO. The two papillomas that were treated with a DHE composition but that did not receive light showed no change. The untreated papilloma control skin regions showed the expected erythema.

These experiments clearly showed the efficacy of topical application of DHE (HPD) in an appropriate solvent when prepared as outlined according to the invention for the treatment of papillomavirus induced disease. In each case where efficacy of the composition was demonstrated, the surrounding normal skin showed no deleterious side effects even after 3 months followup.

What is claimed is:

1. A non-lyophilized topical composition for photodynamic therapy, comprising a photoreactive agent dispersed in a carrier vehicle which is capable of deep penetration when applied to mammalian skin or mucosa.

2. The composition of claim 1, wherein the concentration of said photodynamic agent is from about 1 to about 7.5 mg/ml.

3. The composition of claim 2, wherein the concentration of said photodynamic agent is about 2.5 mg/ml.

4. The composition of claim 2, wherein said photoreactive agent comprises HPD, DHE, or mixtures thereof.

5. The composition of claim 4, wherein said carrier vehicle comprises a hydrophilic gel or cream.

6. The composition of claim 4, wherein said carrier vehicle has a high alcohol content.

7. The composition of claim 6, wherein said carrier vehicle comprises about 50% w/w SD alcohol, the remainder comprising one or more of propylene glycol, purified water, polyoxyethylene lauryl ether dioctyl sodium sulfosuccinate, and the like.

8. The composition of claim 6, wherein said carrier comprises 54% by weight SD alcohol, the remainder comprising propylene glycol, purified water, polyoxyethylene lauryl ether, and dioctyl sodium sulfosuccinate.

9. The composition of claim 4, wherein said carrier vehicle comprises DMSO.

10. The composition of claim 4, wherein said photoreactive agent is capable of destroying areas of abnormal tissue growth when exposed to light having a wavelength of from about 625 to about 635 nm.

11. The composition of claim 10, wherein the abnormal tissue growth is caused by papillomavirus disease.

12. A process for preparing a topical composition for photodynamic therapy, comprising
    (a) concentrating an aqueous solution of a photoreactive agent to from about 20 to about 25% of its original volume; and
    (b) rediluting said agent in a penetrating topical carrier vehicle.

13. The process of claim 12, further comprising placing said agent in a vacuum of from about 20 to about 35 mm Hg at a temperature of from about 5° to about 15° C. during the concentration step.

14. The process of claim 12, further comprising mildly and constantly agitating the mixture of said agent and said carrier during the concentrating step.

15. The process of claim 12, further comprising mildly and constantly agitating the mixture of said agent and said carrier vehicle during the rediluting step.

16. The process according to claim 12, further comprising applying said composition to a diseased area of mammalian skin, and thereafter exposing the area to light having a wavelength in the red spectrum.

17. The process according to claim 16, further comprising exposing the diseased area to light having a wavelength of from about 625 to about 635 nm.

18. The process of claim 12, wherein said photoreactive agent comprises HPD, DHE, or a mixture thereof.

19. The process of claim 18, wherein said carrier vehicle is a hydrophilic gel or cream.

20. The process of claim 19, wherein said carrier vehicle comprises about 50% w/w SD alcohol, the remainder comprising one or more of propylene glycol, purified water, polyoxyethylene lauryl ether dioctyl sodium sulfosuccinate, and the like.

21. The process of claim 20 wherein said carrier vehicle is DMSO.

22. The process of claim 20, wherein said carrier vehicle comprises 54% by weight SD alcohol, the remainder comprising propylene glycol, purified water, polyoxyethylene lauryl ether, and dioctyl sodium sulfosuccinate.

23. The product of claim 13.

24. A process for preparing a topical non-lyophilized composition for the photodynamic treatment of tissue growth caused by papillomavirus disease, comprising slowly evaporating an aqueous solution comprising from about 1 to about 7.5 mg/ml of a hematoporphyrin until it is concentrated to from about 20 to about 25 percent of its original volume; and rediluting the resulting concentration with gentle mixing with a carrier vehicle capable of deeply penetrating mammalian skin or mucosa.

25. The process of claim 24, further comprising vortexing said aqueous solution under vacuum with constant cooling.

26. The process of claim 25, further comprising placing said resulting concentration in an ice bath before rediluting.

27. The process of claim 24, further comprising rediluting the resulting concentrate until it is brought back to its original volume.

28. The process of claim 24, wherein said carrier vehicle comprises DMSO; a composition comprising 54% by weight SD alcohol, the remainder comprising propylene glycol, purified water, polyoxyethylene lauryl ether, and dioctyl sodium sulfosuccinate; or mixtures thereof.

29. The product of claim 24.

30. The product of claim 25.

31. The product of claim 27.

32. A method of topically treating papillomavirus disease comprising applying the product of claims 29, 30 or 31 to an affected area of mammalian skin or mucosa, and irradiating the affected area with red light.

33. A method of topically treating papillomavirus disease comprising slowly evaporating an aqueous solution comprising from about 1 to about 7.5 mg/ml of a hematoporphyrin until it is concentrated to about 20 to about 25 percent of its original volume;

rediluting the resulting concentrate in a carrier vehicle capable of deeply penetrating mammalian skin or mucosa to form a topical composition;

applying the topical composition to an affected area of mammalian skin or mucosa; and irradiating the affected area using light having a wavelength in the red spectrum.

34. The method of claim 33, further comprising placing the aqueous solution in a vacuum of from about 20 to 25 mm Hg at a temperature from about 5° to about 15° C. during the concentration step.

35. The method of claim 34, further comprising vortexing the aqueous solution during the concentration step.

36. The method of claim 35, further comprising placing the resulting concentrate in an ice bath before rediluting.

37. The method of claim 36, wherein the resulting concentrate is rediluted to its original volume.

* * * * *

UNITED STATES PATENT AND TRADEMARK OFFICE
CERTIFICATE OF CORRECTION

PATENT NO. : 4,925,736

DATED : May 15, 1990

INVENTOR(S) : Mark J. Shikowitz

It is certified that error appears in the above-identified patent and that said Letters Patent is hereby corrected as shown below:

Column 1, line 3, insert:

-- This invention was made with government support under Grant NS 19214 and NS 19215 awarded by the National Institutes of Health. The government has certain rights in the invention. --

Signed and Sealed this

Second Day of November, 1993

Attest:

BRUCE LEHMAN

Attesting Officer

Commissioner of Patents and Trademarks